(12) United States Patent
Kawakami et al.

(10) Patent No.: US 6,461,633 B1
(45) Date of Patent: Oct. 8, 2002

(54) REDUCING SUGAR-CONTAINING FAT EMULSION AND A METHOD FOR ITS STERILIZATION

(75) Inventors: Keiichi Kawakami, Tokushima (JP); Katsushi Watanabe, Tokushima (JP); Teru Nakai, Naruto (JP); Katsumi Uei, Naruto (JP); Aya Bandou, Tokushima (JP); Tatsuya Ishii, Toyama (JP); Yuki Hirata, Naruto (JP); Takashi Fujimoto, Tokushima (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/463,309

(22) PCT Filed: Jul. 25, 1997

(86) PCT No.: PCT/JP97/02594

§ 371 (c)(1),
(2), (4) Date: Jan. 24, 2000

(87) PCT Pub. No.: WO99/04799

PCT Pub. Date: Feb. 4, 1999

(51) Int. Cl.[7] ............................................... A61K 47/00
(52) U.S. Cl. ...................... 424/439; 424/400; 424/422; 426/312; 426/316; 426/324; 426/330.1; 426/474
(58) Field of Search ................................ 424/400, 439, 424/422; 426/312, 316, 324, 330.1, 474

(56) References Cited

U.S. PATENT DOCUMENTS 5,674,527 A * 10/1997 Inoue et al. ................ 424/450
5,763,028 A * 6/1998 Matsumoto et al. ........ 428/34.7

FOREIGN PATENT DOCUMENTS

| JP | 2-4671 | 1/1990 |
| JP | 5-9112 | 1/1993 |
| JP | 5-65220 | 3/1993 |
| JP | 5-148149 | 6/1993 |
| JP | 6-336442 | 12/1994 |
| JP | 7-277989 | 10/1995 |
| JP | 8-164186 | 6/1996 |

* cited by examiner

Primary Examiner—Thurman K. Page
Assistant Examiner—Liliana Di Nola-Baron
(74) Attorney, Agent, or Firm—Sughrue Mion, PLLC

(57) ABSTRACT

The invention provides a reducing sugar-containing fat emulsion comprising an oil-in-water fat emulsion available upon emulsification of a fat with an emulsifier wherein a reducing sugar and at least one buffer substance selected from among organic acids with acid dissociation exponents in water within the range of 5.0–7.5 and their salts are concurrently contained in the water phase thereof, with the emulsion having been adjusted to pH 5.0–7.5; a reducing sugar-containing fat emulsion product which comprises a medicinal fluid containing a reducing sugar and a fat as sterilized with carbon dioxide gas dissolved therein and contained in a plastic infusion container, said plastic infusion container being accommodated together with a carbon dioxide gas absorber in a substantially oxygen-impermeable secondary container; and a method for their preparation and sterilization. The reducing sugar-containing fat emulsion is stable and of high quality, because it is inhibited against formation of free fatty acids, decomposition of the reducing sugar, and hence coloration.

12 Claims, 1 Drawing Sheet

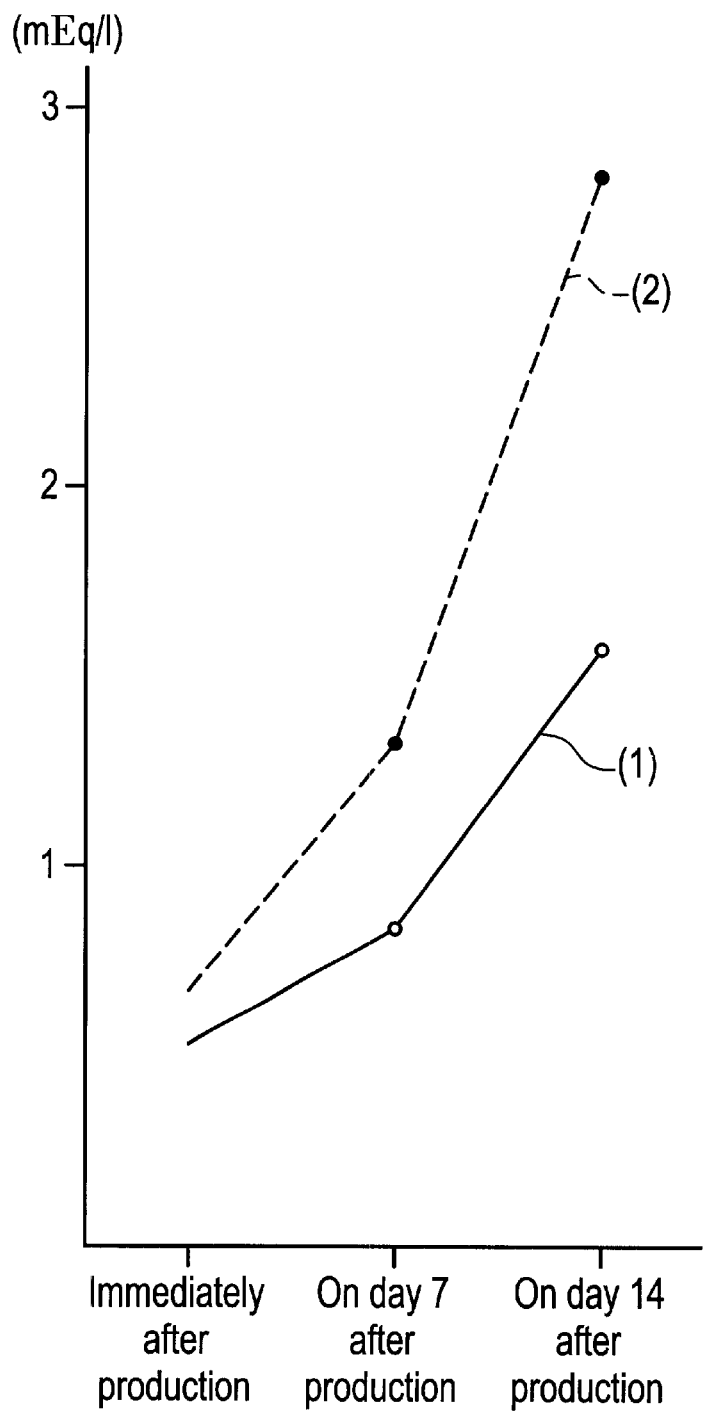

REDUCING SUGAR-CONTAINING FAT EMULSION AND A METHOD FOR ITS STERILIZATION

This application is a 371 of PCT/JP97/02594, filed Jul. 25, 1997.

TECHNICAL FIELD

The present invention relates to a reducing sugar-containing fat emulsion for intravenous injection, such as intravenous hyperalimentation, and more particularly to a high-quality, stable fat emulsion in which the formation of free fatty acids on heat sterilization is minimized despite inclusion of a reducing sugar and which is inhibited against the discoloration due to decomposition of the reducing sugar and to a method for its sterilization.

BACKGROUND ART

Because many patients having undergone a gastrointestinal surgery cannot be orally fed, the nutritional management for such patients is generally secured by intravenous hyperalimentation through a central vein (IVH). This IVH is very effective in upholding the nutritional status of such patients to accelerate recovery and cure and, therefore, in broad use in the field of surgical therapy.

Meanwhile, said IVH calls for strict control over the procedure and has certain demerits such as the risk of infection and that of metabolic complications such as hyperglycemia. Therefore, the recent trend is toward feeding from a peripheral vein as far as possible even in those patients for whom IVH is contraindicated but whose preoperative nutritional status is good and in whom the degree of surgical invasion is comparatively slight and in those patients in whom the expected duration of impossibility of oral feeding is not too long.

In any event, not only the supply of carbohydrates, amino acids, and electrolytes but also the supply of fat is considered indispensable to the nutritional management of patients. Particularly in the feeding through a peripheral vein, it is essential to use a fat emulsion as part of the energy source so that the caloric requirements may be fulfilled while the elevation of the osmotic pressure of the infusion is prevented as much as possible.

Meanwhile, the ideal dosage form for such hyperalimentation, etc. is a one-package dosage form containing all the components to be administered in a single package. However, it is known that a sugar and an amino acid undergo a Meillard's reaction to cause browning and that the concurrent presence of a fat emulsion and an electrolyte, particularly a polyvalent cation, results in aggregation of emulsion particles. Therefore, such components cannot be formulated in the same package, and generally it has been attempted to provide a double-packed dosage form containing a reducing sugar and a fat emulsion in one package and amino acids and electrolytes in another package.

However, an aqueous solution of a reducing sugar such as glucose undergoes depression in pH upon sterilization and with time after sterilization and when the solution is mixed with a fat emulsion, this pH depression induces production of free fatty acids due to hydrolysis of the fat and emulsifier. Such free fatty acids are apparently responsible for the adverse reactions associated with administration of a fat emulsion, such as fever and headache, and therefore, occurrence of free fatty acids should be avoided as far as possible. Thus, the production of free fatty acids due to pH depression upon sterilization is a fatal drawback of such a mixed formulation.

To overcome the above disadvantage, research has been undertaken along several lines of approach but invariably no satisfactory results have been obtained. Thus, it has been attempted (as in Japanese Unexamined Patent Publication No. H5-65220) to prevent increase in the concentration of free fatty acids by incorporating L-histidine and/or tris (hydroxy-methyl)aminomethane as a buffer in a reducing sugar-containing fat emulsion but even this method does not provide for complete inhibition of formation of free fatty acids.

It has also been attempted to solve the above problem by adding a phosphate salt to a reducing sugar-containing fat emulsion at a final concentration of 3 mM to 20 mM (Japanese Unexamined Patent Publication No. H7-277989) but since the emulsion particles tend to aggregate particularly after heat sterilization, the method is not suitable for a stable production and supply of an emulsion of high quality.

In addition, a reducing sugar-containing fat emulsion has the disadvantage that the emulsion becomes tinted by decomposition products of the reducing sugar as formed during heat sterilization and during subsequent storage. This disadvantage can be generally obviated by maintaining the pH of the emulsion at a low level but in view of the fact that the emulsion is to be administered in a large dose, the pH of the product is preferably not removed too far from the pH of the circulating blood.

For this reason, the pH of a reducing sugar-containing fat emulsion is conventionally controlled within the range of about 5–7.5 and, separately from this pH adjustment, a coloration inhibitor, such as dithioglycerol or dithiothreitol, is generally incorporated for preventing the above-mentioned coloration associated with the reducing sugar (e.g. Japanese Unexamined Patent Publication No. H5-9112).

However, addition of any component irrelevant to hyperalimentation and so on, such as said coloration inhibitor, is not desirable but preferably avoided. Moreover, this infusion has the drawback that it has a sulfur odor due to the coloration inhibitor. Therefore, the research and development for a reducing sugar-containing fat emulsion which does not contain a coloration inhibitor and yet is free from the discoloration problem arising from decomposition of a reducing sugar and inhibited against production of free fatty acids has been awaited in earnest by the industry.

The object of the present invention is to develop and provide an improved stable reducing sugar-containing fat emulsion and a production technology for the manufacture thereof, long awaited by the industry, the emulsion simulating the physiological pH, being free from or markedly inhibited against the discoloration due to decomposition of the reducing sugar even without the aid of a coloration inhibitor, being inhibited against production of free fatty acids and not undergoing aggregation of emulsion particles which is a disadvantage of the prior art fat emulsion.

To accomplish the above object, the inventors of the present invention explored into a broad range of buffer substances in the first place and discovered that when a certain organic acid or a salt thereof is used within a certain pH range, the enhanced stability of a reducing sugar-containing fat emulsion is neatly insured.

In addition, the inventors of the present invention found that when the pH of a drug system containing a reducing sugar and a fat emulsion (with pH about 5.0–7.5) is temporarily reduced by dissolving carbon dioxide gas therein prior to heat sterilization and, thereafter, the carbon dioxide gas is removed from the drug system, the decomposition of the reducing sugar during heat sterilization and storage is inhibited and, at the same time, the coloration is inhibited even in the absence of a coloration inhibitor to give a satisfactory reducing sugar-containing fat emulsion.

Furthermore, the inventors of the present invention discovered that said removal of carbon dioxide gas from the drug system after sterilization can be quickly achieved through the use of a carbon dioxide gas absorber and that when such carbon dioxide gas absorber is employed, the adverse effect of oxygen on the drug system is also precluded so that the decomposition of the reducing sugar during sterilization and storage is inhibited to prevent not only discoloration of the emulsion but also production of free fatty acids. The present invention has been developed on the basis of the above findings.

DISCLOSURE OF THE INVENTION

The present invention provides a reducing sugar-containing fat emulsion comprising an oil-in-water fat emulsion available upon emulsification of a fat with the aid of an emulsifier, with a water phase containing a reducing sugar and at least one buffer substance selected from among organic acids with acid dissociation exponents in water within the range of 5.0–7.5 and salts thereof and the pH of the emulsion having been adjusted to a range of 5.0–7.5.

The present invention in another aspect provides a reducing sugar-containing fat emulsion comprising a medicinal fluid containing a reducing sugar and a fat component as sterilized in the condition in which carbon dioxide gas has been dissolved therein is packaged in a plastic infusion container (hereinafter referred to as primary container) which, in turn, is packaged together with a carbon dioxide gas absorber in an outer container which is substantially impermeable to oxygen gas (hereinafter referred to as secondary container).

The present invention, in a further aspect, provides a method of sterilizing a reducing sugar-containing fat emulsion comprising dissolving carbon dioxide gas in a medicinal fluid containing a reducing sugar and a fat and sterilizing the same. The present invention also provides a sterilized reducing sugar-containing fat emulsion made by said method of sterilization.

The fat emulsion as a component of the reducing sugar-containing fat emulsion of the present invention is not different from the fat emulsion conventionally used for intravenous feeding, i.e. an oil-in-water fat emulsion prepared by emulsifying a fat component with an emulsifier.

The fat for use in said emulsion may also be any of the oils and fats used conventionally as calorie sources (energy sources) for hyperalimentation, etc., thus including a variety of vegetable oils such as soybean oil, cottonseed oil, safflower oil, corn oil, coconut oil, perilla oil, styrax oil, linseed oil, etc., fish oils such as sardine oil, cod liver oil, etc., long-chain fatty acid triglycerides (LCT) which are essential fatty acid sources, and medium-chain fatty acid triglycerides (MCT) usually with a carbon number of 8–10, which are characterized by ease of absorption, ease of combustion, and a reduced tendency toward accumulation, such as Panacete™ (NOF Corporation) and ODO™ (The Nisshin Oil Mills, Ltd.) as typical examples. Furthermore, said fat includes chemically defined triglycerides such as 2-linoleoyl-1,3-dioctanoylglycerol, 2-linoleoyl-1,3-didecanoylglycerol, etc. Those substances can be used independently or in combination. The fat is incorporated in the product of the invention preferably in a final concentration of about 1.5–20 w/v % or, for a better result, about 2–8 w/v %.

The emulsifier can also be any of those emulsifiers which are generally used, e.g. phospholipids such as egg yolk lecithin, hydrogenated egg yolk lecithin, soybean lecithin, hydrogenated soybean lecithin, etc. and synthetic surfactants (e.g. commercial products such as Tween 80, HCO-60, Pluronic F68, etc.). The proportion of the emulsifier is not critical but preferably about 30–300 mg per gram of the fat.

The reducing sugar, i.e. another energy source in the reducing sugar-containing fat emulsion of the present invention, may be any of the sugars conventionally used in infusions of this type. Preferred examples are glucose, fructose, and maltose. Those sugars can be used singly or in combination. Addition of said reducing sugar can be carried out in the emulsification stage of a fat emulsion or after emulsification. The proportion of the reducing sugar is generally about 5–50 w/v % and preferably within the range of about 6–25 w/v %. From the standpoint of management of blood sugar, the use of glucose is most preferred. Where necessary, non-reducing sugars such as xylitol, sorbitol, glycerol, etc. may also be incorporated in suitable concentrations in the composition of the invention.

In the pharmaceutical composition of the present invention, it is important to incorporate at least one buffer substance selected from the group consisting of organic acids whose acid dissociation exponents in water are in the range of 5.0–7.5 and their salts. The organic acid for use can be selected from a broad range of aliphatic or aromatic carboxylic acids, sulfonic acids, phosphonic acids, etc. Particularly preferred are carboxylic acids. Those organic acids may be monovalent or polyvalent. To mention specific examples, the organic acid includes succinic acid, malonic acid, glutaric acid, maleic acid, malic acid, etc. Particularly preferred is succinic acid.

The term "acid dissociation exponent" as used herein means the pKa value determined in water at room temperature, and taking a dicarboxylic acid as an example, it means the dissociation exponent for the second phase and in the case of a tricarboxylic acid, the term is used referring to the dissociation exponent for the third phase.

As to the above-mentioned salts of organic acids, alkali metal salts such as sodium salts, potassium salts, etc. and magnesium salts can be mentioned as typical examples.

The amount of the buffer substance should be based on the amounts of fat and reducing sugar and, generally speaking, is preferably in the range of about 0.005–0.05 w/v % based on the total composition.

When said buffer substance is a free acid, the reducing sugar-containing fat emulsion of the present invention is adjusted to pH 5.0–7.5 with an alkali. The alkali that can be used generally for this purpose includes alkali metal hydroxides such as sodium hydroxide and potassium hydroxide. On the other hand, when an organic acid salt is used as said buffer substance, the pH of the emulsion is adjusted to the above-mentioned range with an acid or an alkali. The acid that can be used with advantage includes but is not limited to hydrochloric acid, sulfuric acid, and acetic acid. The alkali may be the same as above. The particularly preferred pH range is 5.5–6.5.

The reducing sugar-containing fat emulsion of the present invention, thus obtained, can be used as it is as a final product. However, in view of the fact that the emulsion is generally used in combination with other components such as amino acids and electrolytes, the fat emulsion is preferably supplied in a double-packaged dosage form such that the emulsion is contained in a compartment of a multi-compartment container provided with a divider normally precluding intercommunication of its compartments and said amino acids and electrolytes are contained in another compartment so that the contents of the two compartments may be mixed by piercing or otherwise disrupting said divider prior to administration.

As examples of said multi-compartment container, there can be mentioned (1) a container provided with an easily separable divider by heat sealing (Japanese Unexamined Patent Publication No. H2-4671, Japanese Unexamined Utility Model Publication No. H5-5138), (2) a container equipped with a divider formed by clipping (Japanese Unexamined Patent Publication No. S63-309263), and (3) a container in which a divider is provided with a communicating device (Japanese Unexamined Patent Publication No. S63-20550). Among them, the first-mentioned container (1) is preferred because it is suited for high production and easy to provide for intercommunication of the compartments.

The above-mentioned container is preferably made of a gas-permeable plastic material such as those conventionally used for medical containers. As specific examples, there can be mentioned polyethylene, polypropylene, polyvinyl chloride, crosslinked ethylene-vinyl acetate copolymer, ethylene-α-olefin copolymer, blends of such polymers, and laminates comprising such polymers.

Filling of components into the respective compartments and sterilization can be carried out by the conventional procedures. For example, the respective component fluids are filled into the compartments under an inert gas such as carbon dioxide or nitrogen gas and, after sealing, the whole is heat-sterilized. The method for heat sterilization includes a variety of known methods such as high-pressure steam sterilization (autoclaving), hot water sterilization, and hot water shower sterilization. Where necessary, this heat sterilization can be carried out in an inert gas atmosphere such as nitrogen gas.

The reducing sugar-containing fat emulsion in the form of an infusion prepackaged in a primary container is preferably further packaged, in the state accommodated in said primary container, together with an oxygen absorber in a gas-impermeable secondary container in order that the degradation and oxidation of the infusion may be prevented more positively. Particularly when a container of the above-mentioned type (1) is employed, it is preferably packaged in the secondary container in the condition folded on itself along said divider so that the divider will not be disrupted by an external pressure to bring the compartments into intercommunication by chance. Moreover, where necessary, the above-mentioned packaging may be carried out by the inert gas fill-packaging method.

The gas-impermeable packaging material suited for the secondary packaging may be any of the known containers with gas barrier properties includes but is not limited to polyethylene terephthalate (PET), polyethylene naphthalate (PEN), ethylene-vinyl alcohol copolymer (EVOH), polyvinylidene chloride (PVDC), nylon, and polyesters. The secondary container is preferably molded from a material selected from among the above-mentioned materials or made of a film or sheet of any of said materials, a laminate film or sheet of such materials, or such a film or sheet with a vapor deposition layer of silica and/or alumina, and is more preferably made of a multi-layer film.

The above-mentioned oxygen absorber includes a variety of known materials such as those containing iron or a compound of iron, such as iron hydroxide, iron oxide, iron carbide, etc., as an active component. Typical commercial products of this type are "Ageless" (manufactured by Mistubishi Gas Chemical), "Moduran" (manufactured by Nippon Kayaku), and "Secur" (manufactured by Nippon Soda).

When the filling in a carbon dioxide gas atmosphere and the heat sterilization in a nitrogen atmosphere after sealing have been carried out, it is advisable to put a carbon dioxide gas absorber in the secondary container in order to thoroughly remove the residual carbon dioxide (in the space and in the medicinal fluid). The carbon dioxide gas absorber mentioned above includes commercial products such as "Wakolime" which is a product of Wako Pure Chemical Industries, "Ageless E" which is a product of Mistubishi Gas Chemical, and "Baralyme", a product of Aica Kogyo.

In the administration of the reducing sugar-containing fat emulsion of the present invention, other components such as vitamins and trace elements (minerals) can be optionally added. Said vitamin includes a variety of vitamins, regardless of whether they are water-soluble or lipid-soluble, such as retinol palmitate, thiamine hydrochloride, riboflavine, pyridoxine hydrochloride, cyanocobalamine, ascorbic acid, cholecalciferol, tocopherol acetate, nicotinamide, calcium pantothenate, folic acid, biotin and phytonadione.

The present invention further provides a reducing sugar-containing fat emulsion such that a medicinal fluid containing a reducing sugar and a fat component as sterilized with carbon dioxide gas having been dissolved therein is present in a plastic infusion container which in turn is accommodated together with a carbon dioxide gas absorber in a substantially oxygen-impermeable secondary container and a method of sterilizing said fat emulsion.

By the above-mentioned sterilization procedure utilizing carbon dioxide gas and utilization of a carbon dioxide gas absorber in accordance with the present invention, a reducing sugar-containing fat emulsion can be provided at a physiological pH and its coloration and formation of free fatty acids can be neatly prevented without the aid of a coloration inhibitor.

Furthermore, by the utilization of an oxygen absorber, the coloration of the infusion and production of free fatty acids can be more positively prevented.

In the above procedure for sterilizing the medicinal fluid with the aid of carbon dioxide gas, except that it is essential to conduct sterilization with carbon dioxide gas having been dissolved therein to depress its pH beforehand, other operating conditions such as sterilization time and temperature may be similar to those used in the conventional sterilization techniques. Preferably, the sterilization is conducted at a temperature of 102–121° C. for 20–60 minutes.

Dissolution of carbon dioxide gas in the medicinal fluid can be typically effected by establishing a carbon dioxide plenum within a preparation tank containing the medicinal fluid until the fluid attains the objective pH and, then, feeding either a mixed gas (e.g. nitrogen gas-carbon dioxide gas, air-carbon dioxide gas, etc.) with a carbon dioxide gas partial pressure conducive to an equilibrium with said pH or carbon dioxide gas alone at a suitable pressure or atmospheric pressure to maintain the pH at the above-mentioned level. Thereafter, the medicinal fluid is distributed into a primary container comprising a plastic infusion container, such as a transfusion bag, an infusion bottle, or the like, and purging the internal atmosphere with a similar mixed gas or carbon dioxide gas and the primary container is then subjected to high-pressure steam sterilization (autoclaving), hot water sterilization, or hot water shower sterilization to complete the desired sterilization. The above-mentioned pH is not so critical only if decomposition of the reducing sugar due to the sterilization procedure can be prevented but generally speaking is preferably within the range of pH about 4–6.5.

In the sterilization method of the invention, the carbon dioxide gas dissolved in the medicinal fluid is gradually released during the sterilization procedure and after the procedure so that the pH of the sterilized infusion is ultimately brought to a level approximating the presterilization pH. Therefore, the pharmaceutical composition of the present invention has the advantage that the risk of degradation due to the formation of free fatty acids due to acidification of the fluid is avoided. Therefore, the plastic infusion bag for holding the infusion of the invention is preferably made of a gas-permeable plastic material conventionally used for medical containers and vessels. Specific examples of such container material have already been mentioned hereinbefore.

When a plastic infusion container holding the medicinal fluid is further packaged in a secondary container with gas barrier properties, the above thorough release of carbon dioxide gas becomes fairly difficult so that the pH of the medicinal fluid continues to be inclined on the acidic side over a protracted time period. Therefore, 5-HMF (5-hydroxymethyl-2-furfural) tends to form from the reducing sugar to increase the risk of formation of free fatty acids.

In the present invention, for positive inhibition of the formation of 5-HMF and free fatty acids, the plastic infusion container holding the sterilized medicinal fluid and a carbon dioxide absorber, optionally as well as an oxygen absorber, are packaged together in a substantially oxygen-impermeable secondary container. By this procedure, the pH of the medicinal fluid can be returned to the pH level prior to dissolution of carbon dioxide gas in a short time, with the result that not only can the pH of the fluid be controlled within the physiological pH range (about 5.0–7.5) but the risk of formation of 5-HMF and production of free fatty acids due to the excessive acidity of the fluid can be prevented.

Furthermore, as the reducing sugar-containing fat emulsion is packaged together with an oxygen absorber in said secondary container, the adverse effect of oxygen entering through the secondary container can be prevented so that said production of free fatty acids can be more positively inhibited and the decomposition of the reducing sugar can also be positively prevented.

The substantially oxygen-impermeable secondary container mentioned above may be any of the known containers with gas barrier properties and the raw material for the container includes but is not limited to polyethylene terephthalate (PET), polyethylene naphthalate (PEN), ethylene-vinyl alcohol copolymer (EVOH), polyvinylidene chloride (PVDC), nylon, and polyesters. The secondary container is preferably molded from a material selected from among the above-mentioned materials or made of a film or sheet of any of said materials, a laminate film or sheet of such materials, or such a film or sheet with a vapor deposition layer of silica or alumina, and is more preferably made of a multi-layer film.

The term "substantially oxygen-impermeable" is used throughout this specification and claims appended thereto in reference to an oxygen permeability of generally not more than about 10 ml/m²·day and preferably not more than about 1 ml/m²·day.

The carbon dioxide gas absorber may be any of the known absorbers of carbon dioxide gas, inclusive of commercial products such as "E200", "E400", and "E500" (all manufactured by Mitsubishi Gas Chemical). There is no particular limitation on the mode of use of such absorbers. In the case of finely divided powders, a necessary amount of the powders can be filled into a gas-permeable small bag and put to use. In the case of beads, rods, and other moldings, they can be used either as filled in such a bag or directly as they are.

The amount of the carbon dioxide gas absorber should at least only be sufficient to absorb 500 ml of carbon dioxide gas with respect to 700 ml of the fluid within the plastic infusion container.

The above-mentioned oxygen absorber, either as it is or as prepackaged in a gas-permeable small bag depending on the mode of use, can be accommodated together with said plastic infusion container (primary container) and carbon dioxide gas absorber in a secondary container. The amount of the oxygen absorber should at least only be sufficient to absorb 200 ml of oxygen with respect to 700 ml of the fluid within the primary container.

The above-mentioned carbon dioxide gas absorber and oxygen absorber need not be independently accommodated only if they are sealed in the space between the primary and secondary containers as separated from the primary container. For example, the two absorbers may be used as mix-packaged in one packet.

The reducing sugar-containing fat emulsion of the present invention can be obtained in the above-described manner. This fat emulsion can be used in the same ways as the conventional infusion product. For example, the secondary package is opened and the inclusion contained in the primary container is used as it is alone or after mixing with other substances such as amino acid preparations. By administering the infusion or mixture to a patient requiring the infusion by the intravenous route, the desired nutritional supplementation can be accomplished.

BRIEF DESCRIPTION OF THE DRAWING

FIG. 1 is a diagrammatic representation of the free fatty acid contents of the fat emulsion of the invention and the control fat emulsion as determined by the method described in Test Example 1.

BEST MODE FOR CARRYING OUT THE INVENTION

The following formulation examples (working examples) and test examples are intended to describe the reducing sugar-containing fat emulsion of the invention in further detail and should by no means be construed as defining the scope of the invention.

EXAMPLE 1

Purified soybean oil, purified egg yolk lecithin, glucose, and succinic acid were added to water for injection and using a TK homomixer, the mixture was subjected to crude emulsification at 65–75° C. for 30 minutes. Then, using a Manton-Gaulin homogenizer (Gaulin, 15M-8TA), this crude emulsion was subjected to 10 cycles (passes) of emulsification at a pressure of 400 kg/cm for fine emulsification. This emulsion was made up to 10 liters and adjusted to pH 6.0 with 1N-sodium hydroxide solution, pressurized with carbon dioxide, and filtered through a 1.2 μm filter. In a carbon dioxide atmosphere, the filtrate was distributed into polyethylene infusion bags which were then heat-sterilized in a nitrogen atmosphere to provide a fat emulsion of the following composition according to the invention.

| | |
|---|---|
| Purified soybean oil | 44.4 g/l |
| Purified egg yolk lecithin | 5.33 g/l |
| Glucose | 114.3 g/l |
| Succinic acid | 0.2 g/l |

Comparative Example 1

A fat emulsion prepared by using the same amount of L-histidine in lieu of succinic acid in Example 1 and adjusted to pH 6 with hydrochloric acid was filtered through a 1.2 μm filter and the filtrate was distributed into polyethylene infusion bags. The filled bags were heat-sterilized to provide a comparative fat emulsion.

Test Example 1

Each of the fat emulsion of the invention as prepared in Example 1 and the comparative fat emulsion prepared in Comparative Example 1 was sealed together with an oxygen absorber and a carbon dioxide gas absorber in a gas-barrier outer bag. After purging the internal air with nitrogen gas, the bag was stored at 60° C. and 75% R.H. Immediately after production and on days 7 and 14 after production, the amount of free fatty acids was determined.

The above determination of free fatty acids was carried out by titrating the n-heptane extract of each test sample with 0.01 N-aqueous sodium hydroxide solution. This titration was carried out using thymol blue solution as indicator in a nitrogen stream. The end point of titration was the time when the red color turned blue.

The results are presented in FIG. 1. In FIG. 1, (1) represents the reducing sugar-containing fat emulsion of the invention and (2) represents the comparative fat emulsion. It is clear from FIG. 1 that compared with the comparative fat emulsion, the production of free fatty acids had been definitely inhibited in the fat emulsion of the invention.

EXAMPLE 2

Distilled water for injection was added to purified soybean oil, purified egg yolk lecithin, glucose, and organic acid (succinic acid) according to the following recipe and using a TK homomixer, the mixture was subjected to crude emulsification at 70° C. for 30 minutes. Then, this crude emulsion was further subjected to fine emulsification in a Manton-Gaulin homogenizer (400 kg/cm$^2$, 10 passes) to provide an emulsion. The emulsion was made up to 10 liters and adjusted to pH 6.0 with 1N-aqueous solution of sodium hydroxide.

| | |
|---|---|
| Purified soybean oil | 44.4 g/l |
| Purified egg yolk lecithin (12% based on soybean oil) | 5.33 g/l |
| Glucose | 114.3 g/l |
| Succinic acid | 0.2 g/l |
| Sodium hydroxide (pH control agent) | q.s. |
| Distilled water for injection | q.s. |

The free top space within the emulsion-preparation tank was pressurized with carbon dioxide gas to bring the emulsion to pH 5.2. Then, the plenum of the tank was supplied with a mixed gas($CO_2$:$N_2$=45:55) with a carbon dioxide partial pressure conducive to an equilibrium with the above-mentioned pH. The emulsion in this condition was filled in infusion bags and with the plenum of each bag replaced with the same mixed gas as above, the bags were sterilized in an autoclave at 110° C. for 40 minutes to provide a reducing sugar-containing fat emulsion of the invention in an infusion dosage form.

Test Example 2

The reducing sugar-containing fat emulsion prepared in Example 2 was stored at 60° C. and 75% R.H. for 14 days and the degree of coloration was monitored.

In this monitoring, the appearance of the sample was grossly inspected and, at the same time, the transmission (T %) at 450 nm of the aqueous fraction obtained by ultrafiltration-centrifugation (Kubota Model KR-180A) of the infusion sample was determined with Shimadzu UV-160.

At the same time, the pH of the sample, the free fatty acid (FFA) content (meq/l) of the sample, and the amount (ppm) of 5-hydroxymethyl-2-furfural, which is a representative decomposition product of the reducing sugar were respectively determined by titrimetry and liquid chromatography.

For reference's sake, the same test was carried out using a control sample prepared by the same procedure as Example 2 except that the dissolution of carbon dioxide gas was omitted, that is to say the plenum of the preparation tank and that of the bag were filled exclusively with nitrogen gas.

The test results for each infusion immediately after preparation and 7 and 14 days of storage are presented below in Table 1.

TABLE 1

| Sample | Parameter | Immediately after sterilization | After 7 days of storage | After 14 days of storage |
|---|---|---|---|---|
| Sample of invention | Appearance | Not colored | Slightly colored | Colored |
| | T % | 99.4 | 97.4 | 95.3 |
| | pH | 5.80 | 5.53 | 5.35 |
| | FFA | 0.53 | 0.84 | 1.56 |
| | 5-HMF | 0.31 | 1.55 | 3.93 |
| Control sample | Appearance | Slightly colored | Colored | Colored |
| | T % | 98.7 | 96.7 | 94.3 |
| | pH | 5.52 | 5.28 | 5.12 |
| | FFA | 0.55 | 1.27 | 2.45 |
| | 5-HMF | 0.29 | 3.11 | 8.04 |

It will be apparent from the above Table 1 that as inferable from its high transmissivity, the reducing sugar-containing fat emulsion of the invention has been markedly inhibited against the formation of 5-HMF and other decomposition products of glucose and is, therefore, of satisfactory quality with an extremely low degree of coloration. It is also inferable that the formation of glucose decomposition products with an sour taste has been minimized. Thus, since the pH of the fat emulsion of the invention returns to the pre-sterilization level upon removal of dissolved carbon dioxide gas, the shift of the emulsion to the acidic side with time is prevented and the formation of free fatty acids during storage can also be prevented.

EXAMPLE 3

Distilled water for injection was added to purified soybean oil, purified egg yolk lecithin, glucose, and organic acid (succinic acid) according to the following recipe and using a TK homomixer, the mixture was subjected to crude emulsification at 70° C. for 30 minutes. This crude emulsion was further subjected to fine emulsification with a Manton-Gaulin homogenizer (400 kg/cm², 10 passes) to provide an emulsion. This emulsion was made up to 10 liters and adjusted to pH 6.0 with IN-sodium hydroxide solution to provide an infusion.

Recipe

| | |
|---|---|
| Purified soybean oil | 44.4 g/l |
| Purified egg yolk lecithin | 6.66 g/l |
| Glucose | 114.3 g/l |
| Succinic acid | 0.2 g/l |
| Sodium hydroxide (pH control agent) | q.s. |
| Distilled water for injection | q.s. |

The top space within the emulsion-preparation tank was pressurized with carbon dioxide gas to adjust the infusion to pH 5.2. Thereafter, this pH was maintained by feeding a mixed gas ($CO_2$:$N_2$=45:55) with a carbon dioxide partial pressure conducive to an equilibrium with the infusion pH and the infusion was filled, in 700 ml aliquots, into infusion bags (made of polyethylene, film thickness 250 μm, capacity 1000 ml). After the atmosphere in the space within each bag was purged with the same mixed gas as above, the bags were sterilized in an autoclave at 110° C. for 40 minutes to provide infusion bags.

After cooling, each infusion bag was placed along with "E500" (Mitsubishi Gas Chemical, a carbon dioxide gas absorber) and "Ageless ZH200" (Mitsubishi Gas Chemical, an oxygen absorber) in a 5-layer [oriented polypropylene (OPP)/nylon/EVOH/nylon/linear low-density polyethylene (LLDPE)] laminate bag (capacity 1500–1600 ml) to provide the product of the invention.

The above product was stored at 25° C. and 60% R.H. for 18 days and the pH of the content infusion and the time course of carbon dioxide gas in the bag were monitored.

The results are presented in Table 2. In Table 2, the pre-sterilization infusion pH and carbon dioxide amount in the bag are also shown.

Also shown in Table 2 are the results for Comparative Product I, which was obtained in the same manner as above except that the inclusion of "E500" was omitted (only "Ageless ZH200" was packaged together with the infusion bag) and the results for Comparative Product II, which was obtained by the method which comprised purging the internal atmosphere of the preparation tank at sterilization and that of the infusion bag with nitrogen gas only (without use of carbon dioxide gas) and omitting the inclusion of "E500" but including "Ageless ZH200".

TABLE 2

| Sample | | Before sterilization | Immediately after sterilization | After 4 days | After 10 days | After 18 days |
|---|---|---|---|---|---|---|
| Product of invention | pH | 5.20 | 5.30 | 5.64 | 5.82 | 5.88 |
| | $CO_2$ fraction (%) | 45.0 | 27.5 | 4.63 | 0.48 | 0.06 |
| Comparative product I | pH | 5.20 | 5.30 | 5.55 | 5.57 | 5.60 |
| | $CO_2$ fraction (%) | 45.0 | 27.5 | 7.47 | 7.19 | 5.86 |
| Comparative product II | pH | 5.96 | 5.59 | — | 5.58 | 5.58 |
| | $CO_2$ fraction (%) | 0.06 | 0.16 | — | 0.02 | 0.02 |

It will be apparent from Table 2 that, in the infusion product according to the invention, the carbon dioxide gas is removed almost completely in about 10 days and the pH of the infusion is increased close to the initial level so that the formation of free fatty acids with time is inhibited.

What is claimed is:

1. A sterilized reducing sugar-containing fat emulsion comprising an oil-in-water fat emulsion produced by:
   (a) emulsifying a fat with an emulsifier, wherein the water phase comprises a reducing sugar and at least one buffer substance selected from the group consisting of an organic acid having an acid dissociation exponent in water of 5.0–7.5 and a salt thereof, and wherein the emulsion is adjusted to a pH within the range of 5.0–7.5;
   (b) adjusting the emulsion to a pH in the range of 4.0–6.5 by dissolving carbon dioxide gas in the emulsion;
   (c) sterilizing the resulting emulsion having carbon dioxide gas dissolved therein; and
   (d) returning the pH of the emulsion to the level prior to dissolution of carbon dioxide gas by releasing or removing carbon dioxide gas from the emulsion.

2. The reducing sugar-containing fat emulsion according to claim 1 wherein the formulating amount of said oil is 1.5–20 w/v %, that of said reducing sugar is 5–50w/v %, and the amount of said emulsifier is 30–300 mg per gram of said fat.

3. The reducing sugar-containing fat emulsion according to claim 1, wherein the reducing sugar is glucose.

4. The reducing sugar-containing fat emulsion according to claim 1, wherein the buffer substance is at least one member selected from the group consisting of succinic acid and its alkali metal salts.

5. The reducing sugar-containing fat emulsion according to claim 1, wherein the proportion of the buffer substance is at a level ranging from 0.005 to 0.05 w/v %.

6. The reducing sugar-containing fat emulsion according to claim 1, as packaged in one compartment of a multi-compartment gas-permeable, flexible plastic container and, after sterilization, further over-packaged together with an oxygen absorber in a gas-impermeable outer container.

7. A reducing sugar-containing fat emulsion comprising a medicinal fluid containing a reducing sugar and a fat as sterilized with carbon dioxide gas dissolved therein and contained in a plastic infusion container, the plastic infusion container being accommodated together with a carbon dioxide gas absorber in a substantially oxygen-impermeable outer container, and the medicinal fluid immediately after dissolution of carbon dioxide gas therein is within the range of pH 4.0–6.5, and before dissolution of carbon dioxide gas and after sterilization is within the range of pH 5.0–7.5.

8. The reducing sugar-containing fat emulsion according to claim 7 wherein an oxygen absorber is further accommodated together with said plastic infusion container and carbon dioxide gas absorber in said secondary container.

9. The reducing sugar-containing fat emulsion according to claim 7, wherein said reducing sugar is at least one member selected from the group consisting of glucose, fructose, and maltose.

10. A method for sterilizing a reducing sugar-containing fat emulsion according to claim 1 comprising:
   (a) emulsifying a fat with an emulsifier, wherein the water phase comprises a reducing sugar and at least one buffer substance selected from the group consisting of an organic acid having an acid dissociation exponent in water of 5.0–7.5 and a salt thereof, and wherein the emulsion is adjusted to a pH within the range of 5.0–7.5;
   (b) adjusting the emulsion to a pH in the range of 4.0–6.5 by dissolving carbon dioxide gas in the emulsion;
   (c) sterilizing the resulting emulsion having carbon dioxide gas dissolved therein; and
   (d) returning the pH of the emulsion to the level prior to dissolution of carbon dioxide gas by releasing or removing carbon dioxide gas from the emulsion.

11. The sterilizing g method according to claim 10, wherein the reducing sugar is at least one member selected from the group consisting of glucose, fructose, and maltose.

12. The reducing sugar-containing fat emulsion according to claim 2, wherein the reducing sugar is glucose.

* * * * *